US009389181B2

(12) United States Patent
Boday et al.

(10) Patent No.: US 9,389,181 B2
(45) Date of Patent: Jul. 12, 2016

(54) METHODS AND APPARATUS FOR DETECTING METALS IN LIQUIDS

(71) Applicant: International Business Machines Corporation, Armonk, NY (US)

(72) Inventors: Dylan J. Boday, Tucson, AZ (US); Jeannette M. Garcia, San Jose, CA (US); James L. Hedrick, Pleasanton, CA (US); Rudy J. Wojtecki, San Jose, CA (US); Thomas Zimmerman, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 29 days.

(21) Appl. No.: 14/298,773

(22) Filed: Jun. 6, 2014

(65) Prior Publication Data

US 2015/0355156 A1     Dec. 10, 2015

(51) Int. Cl.
*G01N 21/59*     (2006.01)
*G01N 21/17*     (2006.01)
*G01N 33/20*     (2006.01)
*G01N 21/33*     (2006.01)

(52) U.S. Cl.
CPC .............. *G01N 21/59* (2013.01); *G01N 21/33* (2013.01); *G01N 33/20* (2013.01); *G01N 2201/061* (2013.01)

(58) Field of Classification Search
CPC ....... G01N 33/20; G01N 33/00; G01N 33/84; G01N 33/50; G01N 21/29; G01N 21/25; G01N 21/17; G01N 21/00
USPC .......................................................... 436/73
See application file for complete search history.

(56) References Cited

U.S. PATENT DOCUMENTS

| | | | |
|---|---|---|---|
| 2,889,277 A | 6/1959 | Hughes | |
| 3,340,232 A | 9/1967 | Smith et al. | |
| 3,598,748 A | 8/1971 | Hirosawa et al. | |
| 3,957,742 A | 5/1976 | Kveton | |
| 4,106,904 A | 8/1978 | Oude Alink et al. | |
| 4,224,417 A | 9/1980 | Hajek et al. | |
| 4,225,481 A | 9/1980 | Wagner | |
| 4,246,160 A | 1/1981 | Wagner et al. | |
| 4,301,262 A | 11/1981 | Wagner et al. | |
| 4,877,451 A | 10/1989 | Winnik et al. | |
| 5,112,796 A | 5/1992 | Iannicelli | |
| 5,185,083 A | 2/1993 | Smigo et al. | |
| 5,674,377 A | 10/1997 | Sullivan, III et al. | |
| 5,830,243 A | 11/1998 | Wolak et al. | |
| 5,863,879 A | 1/1999 | Zirnstein et al. | |
| 7,384,434 B2 | 6/2008 | Malfer et al. | |
| 2008/0305047 A1 | 12/2008 | Raymo et al. | |
| 2009/0039018 A1 | 2/2009 | Jordi et al. | |
| 2009/0258429 A1 | 10/2009 | Raymo et al. | |
| 2009/0277791 A1 | 11/2009 | Vu et al. | |
| 2010/0107476 A1 | 5/2010 | Cosimbescu | |
| 2012/0046191 A1* | 2/2012 | Vu .......................... B82Y 15/00 506/9 |
| 2012/0049308 A1 | 3/2012 | Nishimura et al. | |

FOREIGN PATENT DOCUMENTS

| | | |
|---|---|---|
| CN | 101265255 A | 9/2008 |
| CN | 101270095 B | 1/2012 |
| EP | 0928966 B1 | 2/2010 |
| EP | 2636697 A1 | 9/2013 |
| GB | 928112 A | 6/1963 |
| GB | 1531578 A | 11/1978 |
| WO | 9607660 A1 | 3/1996 |
| WO | 0166614 A2 | 9/2001 |
| WO | 0198388 A1 | 12/2001 |
| WO | 0226849 A1 | 4/2002 |
| WO | 2015051715 A1 | 4/2015 |

OTHER PUBLICATIONS

Wang Yulan and Lu Fengcai, Synthesis and Properties of Poly-1,3,5-Triazines, Polymer Communications, 1984, 7 pages, No. 2, Institute of Chemistry, Academia Sinica, Bejing, 1984.
Margit Hiller and Sergey E. Evsyukov, Laser-Engravable Hexahydrotriazine Polmer Networks, Published Online, Aug. 16, 2002.
Henri Ulrich et al., Reaction of Chloromethyl Ether with Primary Amines, May 1961, pp. 1637-1638.
Hemant S. Patel et al., Studies on Synthesis and Characterization of some Novel Aromatic Copolyesters based on s-Triazine, Iranian Polymer Journal, vol. 14, No. 12, 2005, pp. 1090-1098.
Fabian Suriano et al., Functionalized cyclic carbonates: from synthesis and metal-free catalyzed ring-opening polymerization to applications, Polymer Chemistry, The Royal Society of Chemistry, 2011, pp. 528-533.
John Markoff, Error at IBM Lap Finds New Family of Materials, New York Times, May 15, 2014, 4 pages.
Jeanette M. Garcia et al., Recyclable, Strong Thermosets and Organogels via Paraformaldehyde Condensation with Diamines, Science AAAS, vol. 344, May 16, 2014, pp. 732-735.
D.R. Anderson et al., Thermally resistance polymers containing the s-triazine ring, Journal of Polymer Science Part A-1: Polymer Chemistry, vol. 4, Issue 7, pp. 1689-1702, 1966.
T. Okita, Filter method for the determination of trace quantities of amines, mercaptans, and organic sulphides in the atmosphere, Atmospheric Environment (1967), vol. 4, Issue 1, Jan. 1970, pp. 93-102.
Raquel Lebrero et al., Odor abatement in biotrickling filters: Effect of the EBRT on methyl mercaptan and hydrophobic VOCs removal, Bioresource Technology, Special Issue: Innovative Researches on Algal Biomass, vol. 109, Apr. 2012, pp. 38-45.

(Continued)

Primary Examiner — Christine T Mui
(74) Attorney, Agent, or Firm — Patterson + Sheridan, LLP (57) ABSTRACT

Method and apparatus for detecting metals in a liquid are described. The liquid is contacted with a hexahydrotriazine and/or a hemiaminal material, and a UV absorption spectrum of the material before and after exposure to the liquid is examined to determine whether metals are present in the liquid.

9 Claims, 7 Drawing Sheets

(56) References Cited

OTHER PUBLICATIONS

Elbert, et al. "Conjugate Addition Reactions Combined with Free-Radical Cross-Linking for the Design of Materials for Tissue Engineering," Biomacromolecules 2001, 2, 430-441; Published on Web Mar. 3, 2001.
Ferrar, "Reactions of Formaldehyde With Aromatic Amines," J. Appl. Chem, 14, 1964, 389-399.
Geng, et al., "Nanoindentation behavior of ultrathin polymeric films," Polymer 46 (2005) 11768-11772; Available online Oct. 19, 2005.
Oliver, et al. "Measurement of hardness and elastic modulus by; instrumented indentation: Advances in understanding and; refinements to methodology," J. Mater. Res., vol. 19, No. 1, Jan. 2004, 3-20.
Singh, et al., "Ultrasound mediated Green Synthesis of Hexa-hydro Triazines," J. Mater. Environ. Sci. 2 (4) (2011) 403-406.
Stafford, et al., "A buckling-based metrology for measuring; the elastic moduli of polymeric thin films," Nature Materials_3_Aug. 2004, 545-550;Published online: Jul. 11, 2004.
List of IBM patents or Patent Applications Treated as Related, obtained on Apr. 29, 2015.
PCT/US/ 15/34258, The International Search Report, dated Aug. 26, 2015.
Woitecki et al. "Development of a method for detecting trace metals in aqueous solutions based on the coordination chemistry of hexahydrotriazines." Analyst (online), Jun. 2, 2015, vol. 140, Issue 15, pp. 5184-5189. Internet: http://www.ncbi.nlm.gov/pubmed/26035633 (abstract).
Jones et al. "Computational and Experimental Studies on the Mechanism of Formation of Poly (hexahydrotriazines)s and Poly(hemiaminal)s from Reactions of Amines with Formaldehyde." Organic Letters (online), Oct. 8, 2014, vol. 16, Issue 20, pp. 5502-5505. Internet: http://pubs.acs.org/doi/abs/10.1021/ol50284k (abstract).
PCT/US/ 15/34252, The International Search Report, dated Sep. 14, 2015.

\* cited by examiner

METHODS AND APPARATUS FOR DETECTING METALS IN LIQUIDS

BACKGROUND

The present invention relates to metal detection in fluids, and more specifically, to use of hexahydrotriazine and hemiaminal molecules, oligomers, and polymers derived from aromatic and/or polyether diamines to detect metals in liquids.

Many commercially important processes exist to remove metals from liquids. Metals are routinely removed from water for drinking, for purification of groundwater, and for remediation of toxic sites. Metals are also removed from other liquids, such as polar and non-polar organic liquids. Detecting trace metals often requires costly additives and instrumentation. There is a need in the art for a sensitive cost-effective way to detect trace metals in liquids.

SUMMARY

According to one embodiment of the present invention, a method includes contacting a detection material comprising a PHT material or a PHA material with a liquid containing one or more metals; directing UV radiation through the detection material; before contacting the detection material with the liquid containing the one or more metals, detecting a first UV transmission spectrum of the detection material; while contacting the detection material with the liquid containing metals, or after contacting the detection material with the liquid containing metals, detecting a second UV transmission spectrum of the detection material; comparing the first UV transmission spectrum with the second UV transmission spectrum to determine a change in UV transmission of the detection material; and determining whether metals are present in the detection material based on the change in UV transmission of the detection material. The detection material is a reaction product of an aldehyde and a primary diamine.

According to another embodiment, an apparatus includes a support; a detection material comprising a PHA material or a PHT material disposed on the support; a UV source optically coupled to the detection material; and a UV detector optically coupled to the UV source through the detection material.

DETAILED DESCRIPTION

Hexahydrotriazine (HT) materials and hemiaminal (HA) materials derived from aromatic, aliphatic, and/or polyether diamines may be used as a detection material to detect the presence of metals in a liquid by UV absorption spectroscopy. The detection materials may be single molecule species, oligomers, and/or polymers (i.e., polyhexahydrotriazine, PHT, polyhemiaminal, PHA). The detection materials may be made using an aromatic diamine, a polyether diamine, or a mixture thereof to react with an aldehyde such as formaldehyde. Such detection materials will form a complex with metal ions in a liquid, and the presence of the metal ions will change the UV absorption spectrum of the material in relation to the amount of metal on the polymer material. This change in UV absorption may be directly measured using a UV detector, or a phosphorescent material may be used to indicate changing absorption of UV by the detection material, and the visible emissions of the phosphorescent material may be measured using a visible radiation detector.

Figure 1A:
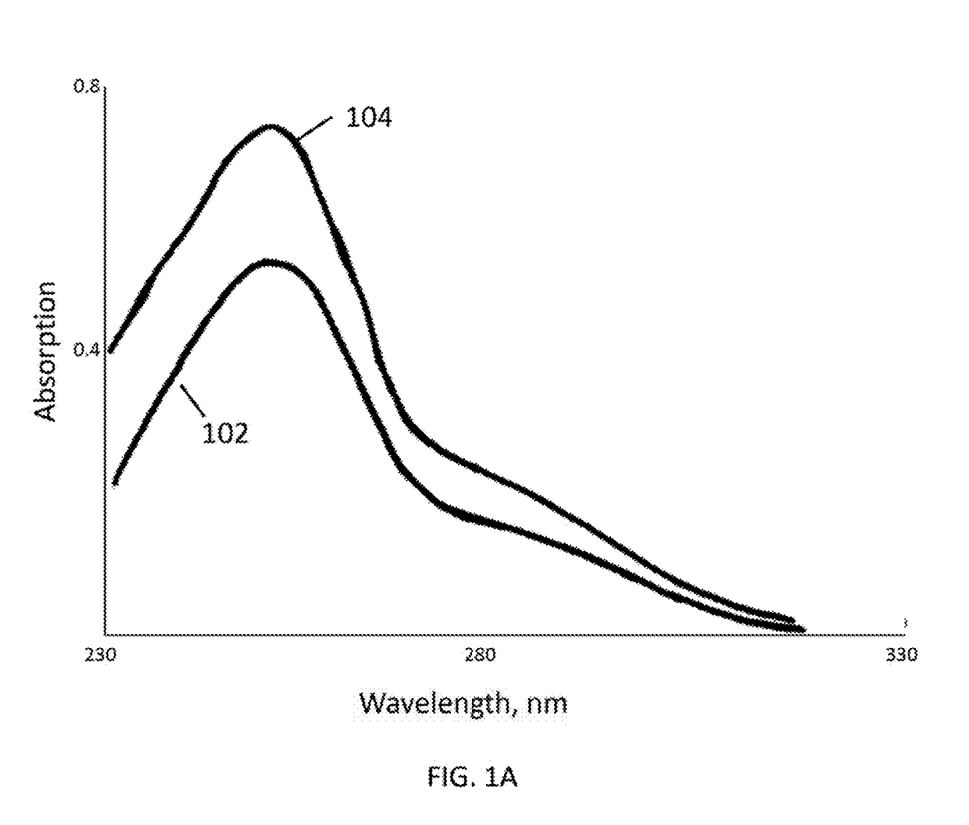
FIG. 1A is a UV spectrograph of a detection material before and after exposure to metal according to one embodiment.

FIG. 1A is a UV spectrograph of an exemplary detection material before and after exposure to metal ions according to one embodiment. The UV absorption spectrum of the detection material before exposure to metal ions is at 102, and the UV absorption spectrum of the same material after exposure to metal ions is at 104. FIG. 1A is representative of the effect of various metals on various different kinds of HT and HA materials. The effect may be seen by exposing an HT or HA material to a liquid for an exposure time, and then exposing the material to UV radiation, for example at a wavelength of 254 nm. The degree of shift in the moderation of radiant energy in the UV absorbance spectrum may be directly or inversely related to the amount of metal deposited on the detection material, but the relation is usually monotonic. In the embodiment of FIG. 1A, the effect of exposing an HT material, 1,3,5-triphenyl-1,3,5-triazinane, to a solution of lithium trifluoromethanesulfonate (also known as "triflate") in 80% acetonitrile, with the balance dichloromethane, on the UV absorption spectrum of the HT material is shown. UV absorption of the HT material increases as metal is added.

Figure 1B:
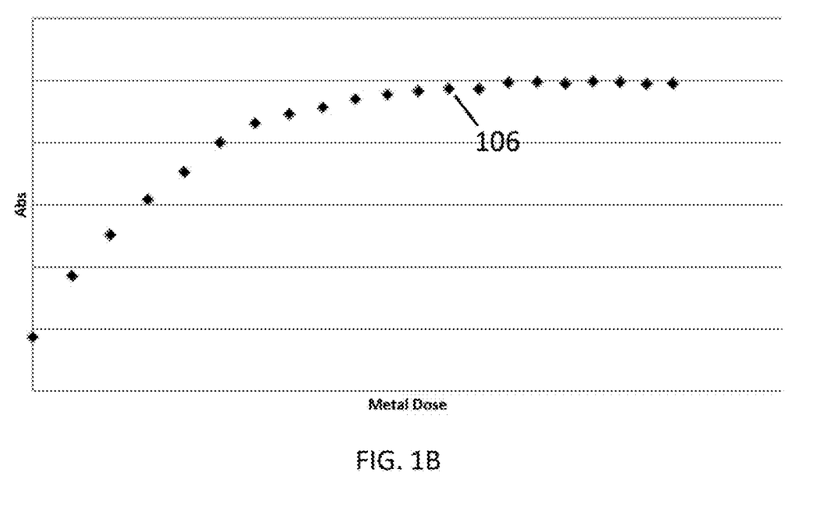
FIG. 1B is a graph showing the effect of increasing lithium dose on UV absorption absorption of a detection material according to another embodiment.

FIG. 1B is a graph showing the effect of increasing dosage of lithium in the mixture above. The data 106 shows monotonically increasing absorption at a wavelength of 251.3 nm with increasing metal dose. A saturation effect is evident.

Figure 1C:
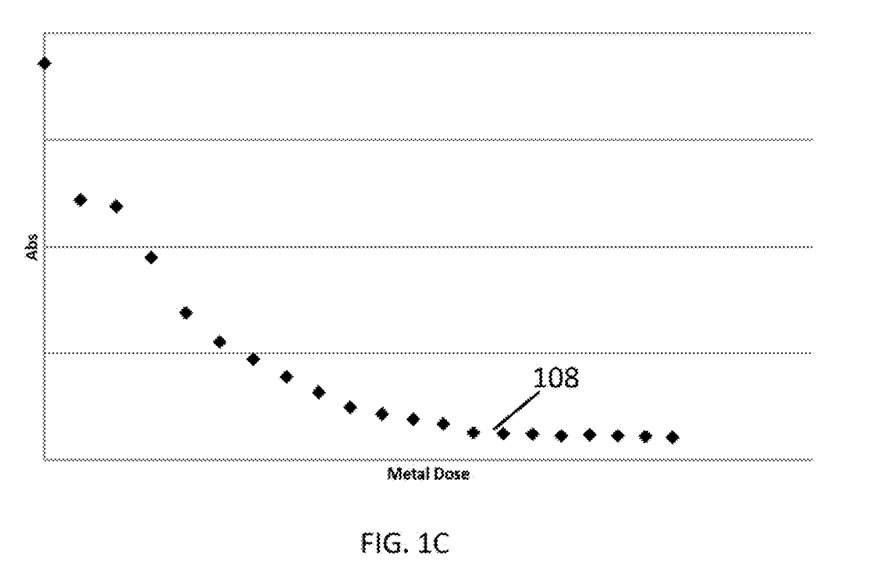
FIG. 1C is a graph showing the effect of increasing europium dose on UV absorption of a detection material according to another embodiment.

FIG. 1C is a graph showing the effect on the same HT material of dosing with europium triflate. The data 108 shows monotonically decreasing absorption at a wavelength of 244.7 nm with increasing metal dose. A saturation effect is also evident in the embodiment of FIG. 1C.

Figure 2:
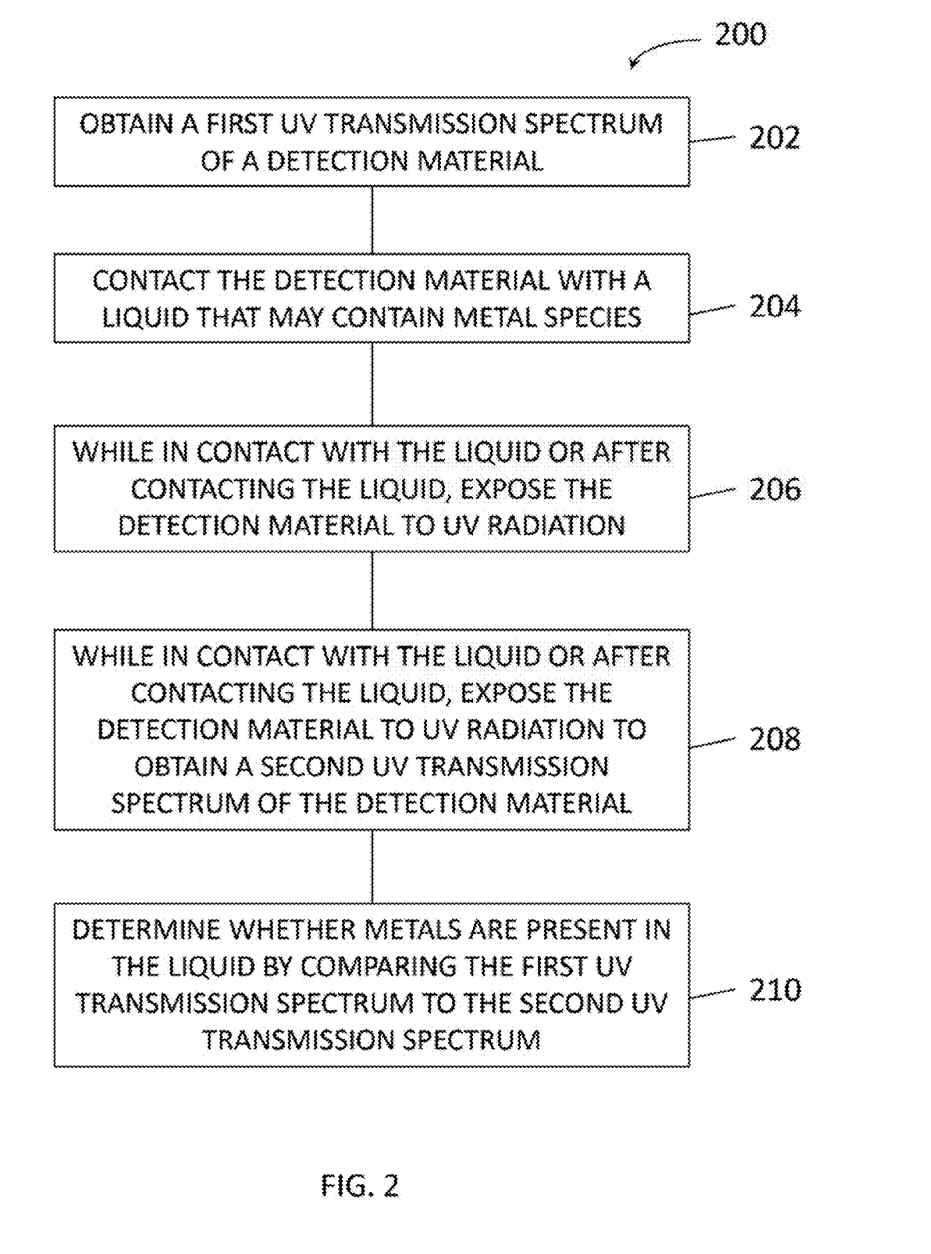
FIG. 2 is a flow diagram summarizing a method of detecting metals in a liquid according to one embodiment.

FIG. 2 is a flow diagram summarizing a method 200 according to another embodiment. A first UV transmission spectrum of a detection material, which may include an HT material or an HA material, or both, is obtained at 202. The detection material may be any of the detection materials described herein, single molecule species, oligomer species, and/or polymer species, and may be structured according to any morphology convenient for recording a UV transmission spectrum. For example, the detection material may be formed into a thin film by depositing a melt or solution of the detection material onto a substrate and allowing the liquid to solidify. The UV radiation is typically radiation having a wavelength or spectrum selected to provide differentiation based on absorption characteristics of the metals of interest.

UV radiation at a wavelength of 200-300 nm may be used, depending on the metals being detected. Specific wavelengths that may be used include 241.3 nm for calcium, 240 nm for silver, 245.3 nm for zinc, 251.3 nm for lithium, and

244.7 nm for europium. Typically a UV source, such as a low pressure mercury vapor lamp, is positioned on one side of the detection material, and a detector on the other side of the detection material. The detector may effectively contact the detection material, or may be spaced apart from the detection material. Typically, the detector will be positioned no more than about 2 mm from the detection material to maximize collection of transmitted radiation. The detection material, and one or more of the UV source and the detector, may be exposed to an inert atmosphere during the UV irradiation, and may be at any desired pressure, including atmospheric pressure, sub-atmospheric pressure, or vacuum. Performing the irradiation at a reduced pressure may reduce effects of the ambient atmosphere on the detected UV radiation in some embodiments.

At 204, the detection material is brought into contact with a liquid that may include one or more metal species such as ions, chelates, compounds, and the like. Typically, the metals are not visibly detectable in the liquid. If the liquid has metal particles, or any other unwanted solid inclusions, the liquid may be filtered before contacting with the detection material. If the solid inclusions do not have a UV absorption property that would interfere with detecting metals in the liquid by UV absorbance changes, the liquid may be contacted with the detection material without filtering.

The detection material may be contacted with the liquid in a number of different ways. One way is to position a film of the detection material for receiving the liquid on a surface of the film and then apply the liquid to the film. The film may be disposed on a support, such as a platform or a rim, and the liquid may be flowed, poured, sprayed, spin applied, ribbon applied, or otherwise applied to the film. In some embodiments, the film may be coated onto, or even adhered onto, a substrate. The film may be coated onto the UV lamp in some embodiments. For example, a UV lamp may be dipped into a liquid that includes a PHT material, and then the liquid may be allowed to solidify on the lamp to form a film. Such a PHT-dipped UV lamp may be used for obtaining the first and/or the second UV transmission spectrum.

In another embodiment, the detection material may be dispersed into the liquid. The detection material may be in a powder form, and may be poured, or otherwise introduced, into the liquid. In some cases, the detection material may be soluble in the liquid. If the detection material is insoluble, or not substantially soluble, in the liquid, the detection material may be removed from the liquid following an exposure period.

It is believed that metals in the liquid may associate with one or more nitrogen atoms in the detection material to produce a complex according to formula (1):

(1)

At 206, the detection material is exposed to UV radiation either while in contact with the liquid or after contact with the liquid to obtain a second UV transmission spectrum. If the liquid contains metals, the detection material will have adsorbed and/or complexed with some of the metal in the liquid, so the composition of the detection material will be different after the liquid exposure from before the liquid exposure. If the detection material is a film, residual liquid may optionally be removed from the film prior to UV exposure by any convenient drying process that does not significantly alter the detection material. If the detection material is a powder, the powder may be removed from the liquid, optionally dried, and prepared for UV exposure in any convenient way, for example by spreading the powder into a thin layer of granules optionally between glass slides. If the detection material is dissolved in the liquid, the UV exposure may be performed on the liquid with the detection material dissolved therein.

At 208, the first UV transmission spectrum is compared to the second UV transmission spectrum to determine whether one or more metals are present in the liquid. Metals from the liquid, adsorbed onto the detection material, alter the UV absorbance spectrum of the material. The difference in the absorbance spectrum is attributable, at least in part, to the adsorbed metals. If the second UV absorption spectrum is obtained in the presence of liquid, any UV absorption by the liquid may additionally be ascertained and separated to determine the presence or absence of metals. The UV absorption attributable to metals is typically compared to a threshold value representing a desired confidence in the presence of metals.

Significant presence of, at least, silver, lithium, calcium, lead, mercury, aluminum, astatine, europium, iron, and cobalt may be detected at 254 nm using the methods and apparatus described herein.

An HT material suitable for forming a film for detecting metals as described herein is a molecule, oligomer, or polymer that has a plurality of trivalent hexahydrotriazine groups having the structure and
a plurality of divalent bridging groups of formula (2):

(2)

wherein L' is a divalent linking group selected from the group consisting of *—O—*, *—S—*, *—N(R')—*, *—N(H)—*, *—R"—*, and combinations thereof, wherein R' comprises at least 1 carbon and R" comprises at least one carbon, each starred bond of a given hexahydrotriazine group is covalently linked to a respective one of the divalent bridging groups, and each starred bond of a given bridging group is linked to a respective one of the hexahydrotriazine groups. In one embodiment, R' and R" are independently selected from the group consisting of methyl, ethyl, propyl, isopropyl, phenyl, and combinations thereof. Other L' groups include methylene (*—$CH_2$—*), isopropylidenyl (*—$C(Me)_2$—*), and fluorenylidenyl:

For PHT materials with bridging groups of formula (2), the PHT may be represented by formula (3):

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (3) is a portion of a different hexahydrotriazine group.

The PHT may also be represented by the notation of formula (4):

wherein x' is moles, L' is a divalent linking group selected from the group consisting of *—O—*, *—S—*, *—N(R)—*, *—N(H)—*, *—R"—*, and combinations thereof, wherein R' comprises at least 1 carbon and R" comprises at least one carbon. Each starred bond of a given hexahydrotriazine group of formula (4) is covalently linked to a respective one of the bridging groups. Additionally, each starred bond of a given bridging group of formula (2) is covalently linked to a respective one of the hexahydrotriazine groups. Polymer molecules may be capped or terminated by a capping group in place of a bridging group in formulas (3) and (4). Examples of capping groups include $CH_3$, hydrogen atoms, ether groups, thioether groups, and dimethyl amino groups.

The PHT or HT can be bound non-covalently to water and/or a solvent (e.g., by hydrogen bonds).

Exemplary non-limiting divalent bridging groups include:

and combinations thereof

A suitable PHT material may be made by forming a first mixture comprising i) one or more monomers comprising two aromatic primary amine groups, ii) an optional diluent monomer comprising one aromatic primary amine group, iii) paraformaldehyde, formaldehyde, and/or another suitable aldehyde, and iv) a solvent, and heating the first mixture at a temperature of at least 150° C., preferably about 165° C. to about 280° C., thereby forming a second mixture comprising a polyhexahydrotriazine. The heating time at any of the above temperatures can be for about 1 minute to about 24 hours. Diamine monomers suitable for making such PHT materials may have the general structure $H_2N$—Ar-L'-Ar—N—$H_2$, where Ar denotes a benzene ring group and L' is defined as described above. Diluent monomers suitable for including in the reaction are typically primary monoamines $RNH_2$, where the group R bonded to nitrogen has a structure according to formula (5), formula (6), formula (7), and/or formula (8):

(5)

(6)

(7)

(8)

wherein W' is a monovalent radical selected from the group consisting of *—$N(R^1)(R^2)$, *—$OR^3$, —$SR^4$, wherein R', $R^2$, $R^3$, and $R^4$ are independent monovalent radicals comprising at least 1 carbon. The starred bonds in formulas (5), (6), (7), and (8) denote bonds with the nitrogen atom of the primary amine monomer. Non-limiting exemplary diluent groups include:

Diluent groups can be used singularly or in combination.

Non-limiting exemplary monomers comprising two primary aromatic amine groups include 4,4'-oxydianiline (ODA), 4,4'-methylenedianiline (MDA), 4,4'-(9-fluorenylidene)dianiline (FDA), p-phenylenediamine (PD), 1,5-diaminonaphthalene (15DAN), 1,4-diaminonaphthalene (14DAN), and benzidene, which have the following structures:

(ODA)

(MDA)

(FDA (PD)

Non-limiting exemplary diluent monomers include N,N-dimethyl-p-phenylenediamine (DPD), p-methoxyaniline (MOA), p-(methylthio)aniline (MTA), N,N-dimethyl-1,5-diaminonaphthalene (15DMN), N,N-dimethyl-1,4-diaminonaphthalene (14DMN), and N,N-dimethylbenzidene (DMB), which have the following structures:

HT and HA detection materials may also be used to detect metals without first forming a film. Small molecules, oligomers, and gels of detection materials may be added to a liquid to expose the detection material to the liquid, and the detection material may then be removed from the liquid and analyzed for UV absorption to determine whether metals are present in the liquid. In some cases, the detection material may also be analyzed for UV absorption in-situ. Some of the detection materials described above may be readily made into films. If a non-film material is used, other kinds of divalent bridging groups may be used to make the detection material. It should be noted that many diamines will react with aldehydes such as formaldehyde to form detection materials. Other exemplary diamines include polyetherdiamines such as polyethylene glycol diamine. Alkyl diamines such as hexane diamine will also react with formaldehyde to form detection materials. The polyether and alkyl derived materials might not readily form films, but gels, oligomers, and small molecules may be formed that are usable as metal detecting materials.

Metal detection may be performed in a continuous-flow mode, a sample-and-test mode. In the continuous-flow mode, a film of PHT material may be exposed to a continuous flow of liquid to allow metals from the liquid to be adsorbed by the PHT material. A UV absorption analyzer may be disposed to direct UV radiation through the film to detect changes in UV absorption as metal is adsorbed onto the film. In a sample-and-test mode, a film, optionally disposed on a support, may be brought to a liquid to be tested and dipped directly in the liquid or in a sample thereof. Alternately, a fixed volume of the liquid may be introduced onto the film, for example by filling a syringe with the liquid and discharging the syringe onto the film.

Figure 3A:
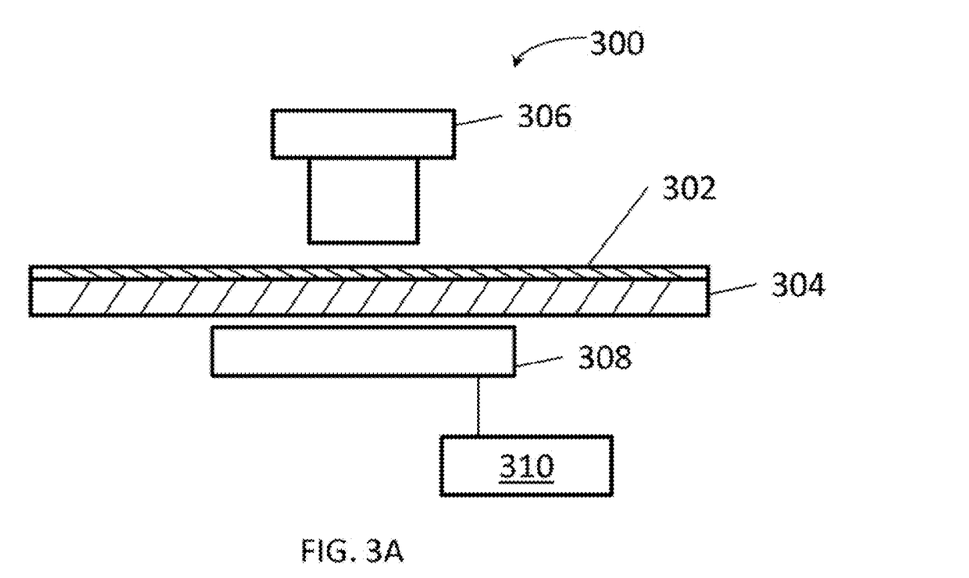
FIG. 3A is a schematic side-view of an apparatus for detecting metals in a liquid according to another embodiment.

FIG. 3A is a schematic side view of an apparatus 300 for detecting metals in a liquid according to one embodiment. The apparatus 300 has a thin film 302 of a PHT material disposed on, or coated on, a support 304. The thin film 302 may be a PHT material having one or more of the divalent linking groups described above, and may have a thickness of about 10 μm to about 500 μm. The thin film 302 may be adhered to the support 304, or the thin film 302 may be removably disposed on the support 304.

The support 304 is typically a structurally strong member that holds the thin film 302 in a configuration to accept UV irradiation through the film. The support 304 may be a continuous or discontinuous material, and the support 304 may be a unitary object or a non-unitary object. Typically, the material of the support 304 is selected to have a minimal UV absorption characteristic, or a UV absorption characteristic that can be separated, minimized, or removed. Thus, the support 304 may be a continuous substrate, such as a sheet or plate, made of a material that does not have a significant UV absorption at the wavelength or spectrum to be used for metal detection. Such materials may include UV transparent glass, such as fused silica or quartz, or polymer, such as cell cast acrylic, or a mixture thereof. Alternately, the support 304 may be a mesh or grid with openings that provide unimpeded transmission of UV radiation transmitted by the thin film 204. The mesh may be metal or polymer.

A UV source 306 is disposed facing the thin film 302. As noted above, the UV source may emit any desired wavelength, and 254 nm radiation is one usable wavelength. The UV source may be a lamp, such as a low pressure mercury vapor lamp, an LED, a laser, or any other UV emitter, or a collection of emitters, which may be a combination of any of the foregoing emitters. An optional optical system 208 may be used to translate the radiation emitted by the UV source to the thin film 302 with minimal dispersion. The optical system may include any combination of fiber optics, light pipes, refractive and reflective elements, lenses, mirrors, retroreflectors, and the like. The UV radiation may be focused, collimated, or otherwise shaped to provide a desired irradiance or fluence for resolving the difference between the original detection material and the metal-exposed detection material.

A UV detector 308 is disposed to receive UV radiation transmitted by the thin film 302. The detector 308 may be opposite the thin film 302 from the UV source, or the detector 308 may be displaced to a convenient location and an optional optical system 210 including any combination of fiber optics, light pipes, refractive and reflective elements, lenses, mirrors, retroreflectors, and the like may be used to translate the transmitted UV radiation to the UV detector 308. The transmitted UV radiation may also be focused, collimated, or shaped in any desired way. In one exemplary embodiment, the support 304 is a mesh, and one or more fiber optics are disposed each with a first end in an opening of the mesh and a second end, opposite the first end, coupled to the UV detector 308.

In one embodiment, the support 304 may be a cylindrical or frustroconical component, and the thin film 302 may be disposed around an outer surface of the support 304. The resulting assembly may be housed inside a UV transparent conduit that surrounds the film to form an annular passage between the film and the conduit. A UV source may be disposed inside the support 304 to direct radiation through the film in a cylindrical pattern, and a UV detector, which may be a detection array such as a photodiode array or CCD array, may be disposed around the outside of the conduit. The resulting detection apparatus may be connected into a pipe or tube to allow continuous flow of a liquid through the annular passage so that continuous monitoring of the liquid for metals may be performed. If two such detection apparatus are connected in parallel using appropriate valving, flow may be switched from one to the other as the detection material of one detector becomes saturated, so that monitoring can continue while the saturated detector is changed.

In this application, the word "transparent" means all, or nearly all, for example about 90% or more, of incident radiation is transmitted at one or more wavelengths of interest. "UV transparent" therefore means that all, or nearly all, for example about 90% or more, incident radiation is transmitted at one or more wavelengths generally accepted as being in the "ultraviolet" range, typically about 100 nm to about 400 nm. An article described herein as "transparent" to some form of radiation is capable of transmitting at least a portion of radiation incident at a first location or surface of the article through at least a portion of the article to a second location or surface of the article such that the radiation exits the article at the second location or surface, and such that the exiting radiation has an intensity at least about 90% of the intensity of the incident radiation.

In the embodiments described above, the support is between the UV source and the UV detector. In other embodiments, the UV detector 308 may be disposed on or in a surface of the support 304 between the support 304 and the thin film 302, such that the UV detector 308 is between the UV source 306 and the support 304. In such an embodiment, the support 304 may be partially or completely opaque to UV radiation. If the UV detector 308 has a thickness larger than can be tolerated between the surface of the support 304 and the thin film 302, a recess may be formed in the surface of the support 304 so that any disruption in the topology of the thin film 302 may be minimized. In any such embodiment, power or data lines may be coupled to the UV detector 308 through the support 304 by forming a passage through the support 304 behind the UV detector 308.

The UV detector 308 may be coupled to a computer system 310 for recording, rendering, analyzing, controlling, storing, transmitting by wire and/or wireless means, and/or providing notifications based on data from the UV detector.

Figure 3B:
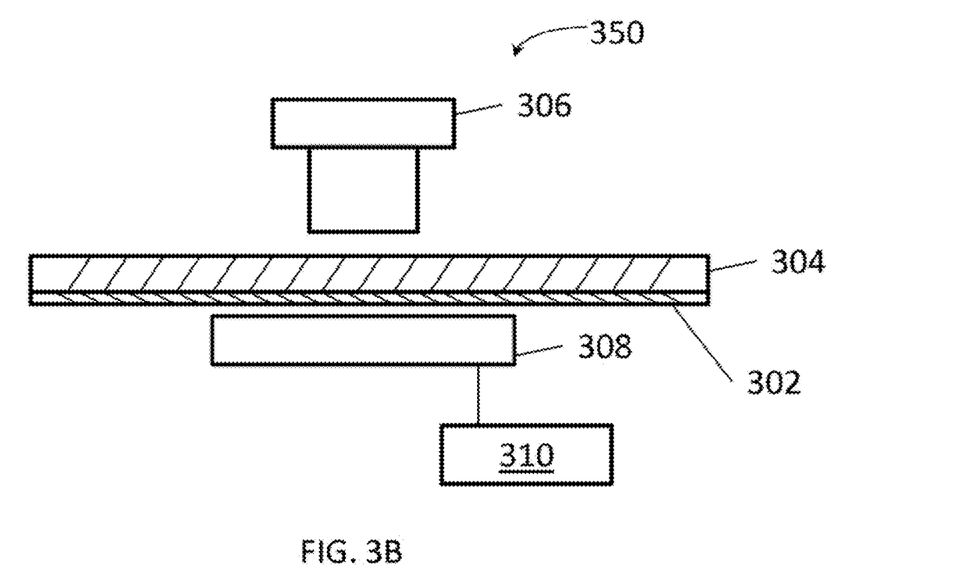
FIG. 3B is a schematic side-view of an apparatus for detecting metals in a liquid according to another embodiment.

FIG. 3B is a schematic side view of an apparatus 350 for detecting metals in a liquid according to another embodiment. The apparatus 350 is substantially the same as the apparatus 300, except that the positions of the support 304 and the thin film 302 are reversed. In the apparatus 350, the support 304 is between the film 302 and the UV source 306. In the apparatus 300 and 350, the support 304 and the thin film 302 may together form a detector element that may be removable and/or replaceable.

Figure 3C:
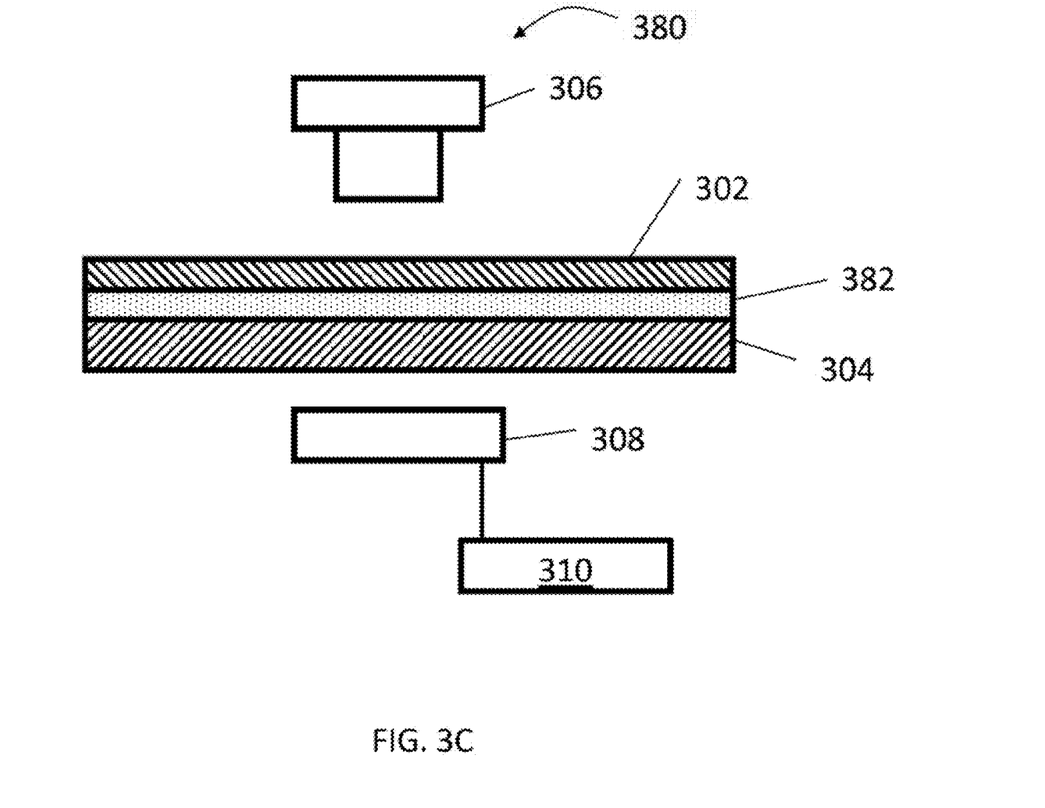
FIG. 3C is a schematic side-view of an apparatus for detecting metals in a liquid according to another embodiment.

FIG. 3C is a schematic side view of an apparatus 380 for detecting metals in a liquid according to another embodiment. The apparatus 380 is substantially the same as the apparatus 300, with the addition of a fluorescent indicator 382 between the thin film 302 and support 304. The fluorescent indicator 382, such as manganese-doped zinc silicate, is excited by UV radiation that is not absorbed by the film 302 and emits visible radiation that passes through the support 304 and into detector 308. In this embodiment, the support can be any material that is substantially transparent to visible radiation, such as borosilicate glass, polycarbonate, or polyethylene terephthalate (PET). The detector 308 is sensitive to visible radiation, for example in the range of 400 to 550 nm wavelength, such as a photodiode or phototransistor. To avoid any chemical interaction among the fluorescent indicator 382, thin film 302 and the liquid that may contain metal species, the fluorescent indicator 382 may be physically separated from the thin film 302 and said liquid, in an exemplary embodiment by casting the fluorescent indicator 382 in poly(methyl methacrylate) (PMMA). Another method of isolation is to include a thin sheet of chemically inert material (not shown) that is substantially transparent to UV radiation between the fluorescent indicator 382 and thin film 302, such as a thin sheet of PMMA. It should be noted, that the orientation of the apparatus 300, 350, and 380 may be horizontal, as shown, or vertical, or any desired angle between horizontal and vertical, and the various supports, films, and layers may be flat, as shown, curved, or angled according to any desired configuration.

Figure 3D:
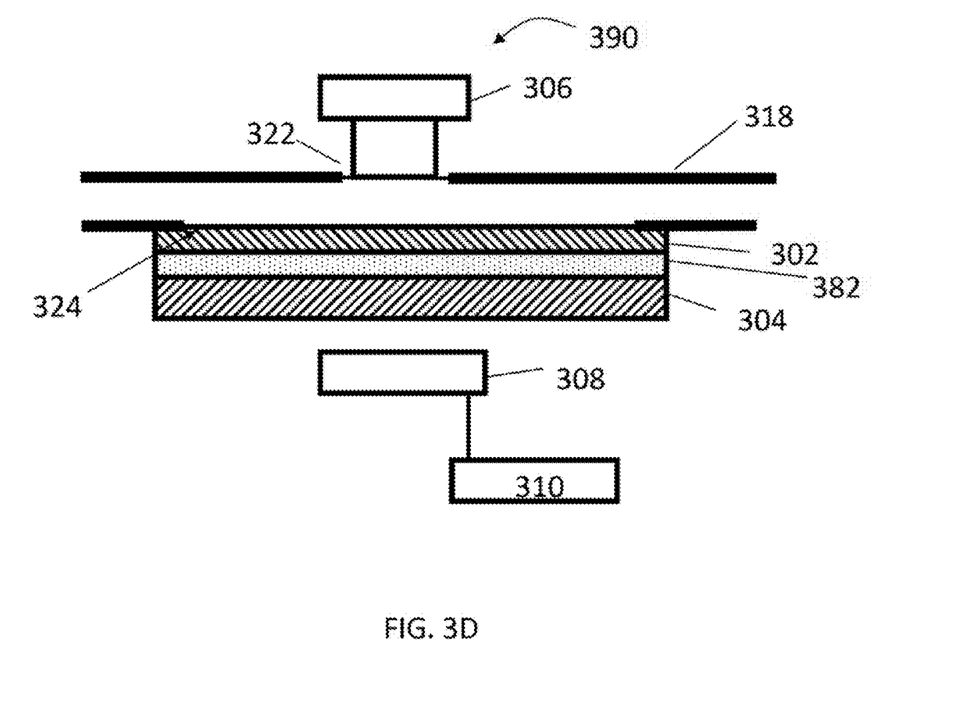
FIG. 3D is a schematic side-view of an apparatus for continuously detecting metals in a liquid according to one embodiment.

FIG. 3D is a schematic side-view of an apparatus 390 for continuously detecting metals in a liquid according to one embodiment. The apparatus 390 incorporates the detection element of the apparatus 380 in a continuous flow configuration. A conduit 318 carries a liquid to be monitored continuously for the presence of metal. The conduit 318 has an opening 324 that is sealed by the thin film 302, which is disposed on the support 304, optionally with the fluorescent indicator 382 between the thin film 302 and the support 302 as in the apparatus 380 of FIG. 3C. The conduit 318 may be a pipe, a tube, or any other liquid transport or flow conduit. The thin film 302 contacts the liquid through the opening 324, and any metals in the liquid are adsorbed onto the thin film 302. UV radiation is emitted continuously or discontinuously from the UV source 306 through a window 322 in a wall of the conduit 318. The window 322 may be covered with a UV transparent material to maintain containment of the liquid in the conduit. The UV radiation passes through the flowing liquid, through the thin film 302, through the optional fluorescent indicator 382, and is detected by the radiation detector 308. The conduit 318 may have a valve or other flow blockage device, if desired, to stop flow of the liquid temporarily in order to replace the thin film 302 or any part of the detector assembly comprising the thin film 302, the optional fluorescent indicator 382, and the support 304. Alternately, two detection apparatus such as the apparatus 390 may be configured in parallel flow so that flow of the liquid may be diverted to a second detector through a second conduit while a first detector in a first parallel conduit is maintained. Alternately, suitable piping and valving may be provided such that, in the event the thin film 302 becomes saturated with metals, flow of the liquid may be stopped and a recharging fluid may be flowed through the conduit 318 to recharge the thin film. The recharging fluid may be a basic solution, such as a 1M solution of NaOH in water, that removes the metal from the thin film 302. Recharging can be monitored using the radiation detector 308, so that when UV absorption returns to a baseline value, the recharging fluid may be stopped and flow of the test liquid reestablished.

In one embodiment, the support 304 may be a cylindrical or frustoconical component, and the thin film 302 may be disposed around an outer surface of the support 304. The resulting assembly may be housed inside a UV transparent conduit that surrounds the film to form an annular passage between the film and the conduit. A UV source such as any of those described above may be disposed inside the support 304 to direct radiation through the film in a cylindrical pattern, and a UV detector, which may be a detection array such as a photodiode array or CCD array, may be disposed around the outside of the conduit. The fluorescent indicator 382 may be disposed around the UV transparent conduit, if desired, and a visible radiation detector may be used. The resulting detection apparatus may be connected into a pipe or tube to allow continuous flow of a liquid through the annular passage so that continuous monitoring of the liquid for metals may be performed. If two such detection apparatus are connected in parallel using appropriate valving, flow may be switched from one to the other as the detection material of one detector becomes saturated, so that monitoring can continue while the saturated detector is changed.

Detection materials described above may be soluble to some extent in the liquid being analyzed. The detection materials may additionally be functionalized to affect solubility in various liquids. For example, a bridging group L' that has hydroxyl groups may be used to increase aqueous solubility or affinity. Alternately, or additionally, substituents of the aromatic rings in the diamine or monoamine reactants may include hydroxyl groups to increase aqueous solubility or affinity. Likewise, hydrocarbon bridging groups L' will tend to increase solubility or affinity for hydrocarbon liquids.

A related material that may be used to detect metals in liquids is a hemiaminal (HA) material. A polyhemiaminal (PHA) is a crosslinked polymer comprising i) a plurality of trivalent hemiaminal groups of formula (9):

(9)

covalently linked to ii) a plurality of bridging groups of formula (10):

(10)

wherein y' is 2 or 3, and K' is a divalent or trivalent radical comprising at least one 6-carbon aromatic ring. In formulas (9) and (10), starred bonds represent attachment points to other portions of the chemical structure. Each starred bond of a given hemiaminal group is covalently linked to a respective one of the bridging groups. Additionally, each starred bond of a given bridging group is covalently linked to a respective one of the hemiaminal groups.

As an example, a polyhemiaminal can be represented by formula (11):

(11)

In this instance, each K' is a trivalent radical (y'=3) comprising at least one 6-carbon aromatic ring. It should be understood that each nitrogen having two starred wavy bonds in formula (11) is a portion of a different hemiaminal group.

The structure of formula (11) can also be represented using the notation of formula (12):

(12)

wherein x' is moles and each bridging group K' is a trivalent radical (y'=3 in formula (10)) comprising at least one 6-carbon aromatic ring. It should be understood that each starred nitrogen bond of a given hemiaminal group of formula (12) is covalently linked to a respective one of the bridging groups K'. Additionally, each starred bond of a given bridging group K' of formula (13) is covalently linked to a respective one of the hemiaminal groups.

Non-limiting exemplary trivalent bridging groups for HA materials include:

The bridging groups can be used singularly or in combination.

Polyhemiaminals composed of divalent bridging groups K' can be represented by formula (13):

wherein K' is a divalent radical (y'=2 in formula (10)) comprising at least one 6-carbon aromatic ring. Each nitrogen having two starred wavy bonds in formula (13) is a portion of a different hemiaminal group.

More specific divalent bridging groups have the formula (14):

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. In an embodiment, R' and R" are independently selected from the group consisting of methyl, ethyl, propyl, isopropyl, phenyl, and combinations thereof. Other L' groups include methylene (*—CH$_2$—*), isopropylidenyl (*—C(Me)$_2$—*), and fluorenylidenyl:

Polyhemiaminals composed of divalent bridging groups of formula (14) can be represented herein by formula (15):

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (15) is a portion of a different hemiaminal group.

The polyhemiaminal of formula (15) can also be represented by the notation of formula (16):

(16)

wherein x' is moles, and L' is a divalent linking group selected from the group consisting of *—O—*, *—S—*, *—N(R')—*, *—N(H)—*, *—R"—*, and combinations thereof, wherein R' and R" independently comprise at least 1 carbon. Each starred nitrogen bond of a given hemiaminal group of formula (16) is covalently linked to a respective one of the bridging groups. Additionally, each starred bond of a given bridging group of formula (16) is covalently linked to a respective one of the hemiaminal groups.

The hemiaminal groups can be bound non-covalently to water and/or a solvent. A non-limiting example is a hemiaminal group that is hydrogen bonded to two water molecules as shown in formula (17):

(17)

In some embodiments, a hemiaminal material may form a covalent network with water molecules that may be a polyhemiaminal hydrate (PHH). A PHA material of this form may be made, for example, by reaction of polyethylene glycol oligomers with paraformaldehyde. Such materials may be organogels in some cases.

Typical HT and HA polymers and oligomers, and PHH materials, as described herein may be disassembled in aqueous solutions. HT oligomers and polymers will disassemble into monomers and may dissolve in acid solutions having pH less than about 3, such as less than about 2.5, for example less than about 2. PHH materials may disassemble into monomers in neutral water. Such properties may be useful in regeneration of detection material that has been saturated with metal due to use over an extended period of time. The detection material may be washed with a solution of appropriate pH to remove any portion of the detection material saturated with metals and expose portions with lower, or zero, metal loading, thus regenerating the detection material. In embodiments with a removable detection element, a used detection element may be replaced with a new detection element, and the used detection element may be subjected to a regeneration process including exposure to an aqueous wash solution of appropriate pH. Alternately, metals may be removed from the detection materials described herein by exposure to a basic solution.

An HA material suitable for use according to the methods described herein may be made using the same groups of reactants as for the HT materials. The diluent monomers described above may also be used to make HA materials. A method of preparing a polyhemiaminal (PHA) comprising divalent bridging groups comprises forming a first mixture comprising i) a monomer comprising two or more primary aromatic amine groups, ii) an optional diluent monomer comprising one aromatic primary amine group, iii) paraformaldehyde, and iv) a solvent. The first mixture is then preferably heated at a temperature of about 20° C. to about 120° C. for about 1 minute to about 24 hours, thereby forming a second mixture comprising the PHA. In an embodiment, the monomer comprises two primary aromatic amine groups. The mole ratio of paraformaldehyde:total moles of primary aromatic amine groups (e.g., diamine monomer plus optional monoamine monomer) may be about 1:1 to about 1.25:1, based on one mole or equivalent of paraformaldehyde equal to 30 grams. The solvent can be any suitable solvent. Exemplary solvents include dipolar aprotic solvents such as, for example, N-methyl-2-pyrrolidone (NMP), dimethylsulfoxide (DMSO), N,N-dimethylformamide (DMF), N,N-dimethylacetamide (DMA), Propylene carbonate (PC), and propylene glycol methyl ether acetate (PGMEA).

A PHT material may be prepared from a PHA material. The PHT can be prepared by heating a solution comprising the PHA at a temperature of at least 150° C., such as about 165° C. to about 280° C. or about 180° C. to about 220° C., for example at about 200° C. for about 1 minute to about 24 hours. Additionally, a mixed PHA/PHT copolymer may be made by partially converting a PHA material to a PHT material. A combination of low conversion temperature, for example about 150° C. to about 165° C., and short conversion time, for example about 1 minute to about 10 minutes, may be used to make a mixed PHA/PHT material.

An exemplary PHA material may be made by reaction of 4,4'-oxydianiline (ODA) with paraformaldehyde (PF). The product is a powder.

A second exemplary PHA material may be prepared by reaction of 4,4'-methylenedianiline (MDA) with PF:

4,4'-Oxydianiline (ODA, 0.20 g, 1.0 mmol) and paraformaldehyde (PF, 0.15 g, 5.0 mmol, 5 equivalents (eq.)) were weighed out into a 2-Dram vial inside a $N_2$-filled glovebox. N-methylpyrrolidone (NMP, 6.2 g, 6.0 mL, 0.17 M) was added. The vial was capped but not sealed. The reaction mixture was removed from the glovebox, and heated in an oil bath at 50° C. for 24 hours (after approximately 0.75 hours, the polymer begins to precipitate). The polyhemiaminal P-1 was precipitated in acetone or water, filtered and collected to yield 0.22 g, >98% yield as a white solid.

ODA was substituted with 4,4'-methylenedianiline (MDA) and a mole ratio of MDA to PF of 1:5 was used. Solid yield of 0.15 g, 69%, was an amorphous, insoluble off-white powder.

A PHT material may be prepared by reaction of ODA and PF, as follows:

P-4, a polyhexahydrotriazine, was prepared by reaction of 4,4'-oxydianiline (ODA) with paraformaldehyde (PF). ODA (0.20 g, 1.0 mmol) and PF (0.15 g, 5.0 mmol, 2.5 eq.) were weighed out into a 2-Dram vial inside a $N_2$-filled glovebox. NMP (6.2 g, 6.0 mL, 0.17 M) was added. The reaction mixture was removed from the glovebox, and heated in an oil bath at 200° C. for 3 hours (after approximately 0.25 hours, the polymer begins to gel in the NMP). The solution was allowed to cool to room temperature and the polymer was precipitated in 40 mL of acetone, allowed to soak for 12 hours, then filtered and dried in a vacuum oven overnight and collected to yield 0.21 g, 95% yield of P-4 as an off-white solid.

The detection materials described herein may be included in a composite material that may be used as a detection material in any of the embodiments described herein. Any desired blend material for a composite may be added to the reaction mixture of diamine and aldehyde prior to formation of a reaction product. For example, reactants may be mixed at a non-reacting temperature, for example less than about 50° C. for some embodiments, and a solid polymer material, for example a powder, a fiber aggregate, or a nanotube aggregate, may be added. The resulting combination may be mixed as the temperature is increased to form a reaction product. Any desired polymer may form a composite material with an HA, HT, or PHH material to provide selected properties. Carbon nanotubes may form a composite with HA, HT, or PHH materials. Polyolefin polymers may also form composite materials with a HA, HT, or PHH material. Such composite materials may be used as detection materials for detecting metals in liquids in some embodiments.

While the foregoing is directed to embodiments of the present invention, other and further embodiments of the invention may be devised without departing from the basic scope thereof, and the scope thereof is determined by the claims that follow.

What is claimed is:

1. An apparatus, comprising:
   a support;
   a detection material comprising a PHA material or a PHT material disposed on the support;
   a UV source optically coupled to the detection material; and
   a radiation detector positioned to receive radiant energy moderated by the detection material.

2. The apparatus of claim 1, further comprising a liquid source fluidly coupled to the detection material.

3. The apparatus of claim 1, wherein the radiation detector is a UV detector optically coupled to the UV source through the detection material.

4. The apparatus of claim 1, further including a fluorescent indicator to receive UV radiation from the UV source passing through the detection material and emit visible radiation.

5. The apparatus of claim 4, wherein the detection material is between the UV source and the fluorescent indicator.

6. The apparatus of claim 4, wherein the fluorescent indicator is between the detection material and the radiation detector.

7. The apparatus of claim 3, wherein the detection material is a film adhered to the support.

8. The apparatus of claim 7, wherein the support is between the UV source and the film.

9. The apparatus of claim 4, wherein the detection material is adhered to the support.

* * * * *